United States Patent [19]

Sweet

[11] Patent Number: 5,162,410
[45] Date of Patent: Nov. 10, 1992

[54] HOT-MELT SILICON PRESSURE SENSITIVE ADHESIVES WITH PHENYL-CONTAINING SILOXANE FLUID ADDITIVE AND RELATED METHODS AND ARTICLES

[75] Inventor: Randall P. Sweet, Midland, Mich.

[73] Assignee: Dow Corning Corporation, Midland, Mich.

[21] Appl. No.: 809,236

[22] Filed: Dec. 17, 1991

Related U.S. Application Data

[63] Continuation of Ser. No. 508,459, Apr. 13, 1990, abandoned.

[51] Int. Cl.$^5$ .............................................. C08K 5/54
[52] U.S. Cl. .................................. 524/266; 524/268; 524/588; 525/477; 427/387
[58] Field of Search ............... 524/266, 268, 588; 525/477; 427/387

[56] References Cited

U.S. PATENT DOCUMENTS

| | | | |
|---|---|---|---|
| 3,954,692 | 5/1976 | Downey | 260/33.6 AQ |
| 4,001,167 | 1/1977 | Tungseth et al. | 260/33.6 AQ |
| 4,038,346 | 7/1977 | Feeney | 260/887 |
| 4,064,094 | 12/1977 | Downey | 260/328 A |
| 4,253,460 | 3/1981 | Chen et al. | 128/283 |
| 4,335,026 | 6/1982 | Balinth | 524/271 |
| 4,427,737 | 1/1984 | Cilento et al. | 428/315.7 |
| 4,551,490 | 11/1985 | Doyle et al. | 524/22 |
| 4,634,629 | 1/1987 | Inaba et al. | 428/343 |
| 4,680,333 | 7/1987 | Davis | 524/394 |
| 4,699,816 | 10/1987 | Galli | 428/40 |
| 4,714,655 | 12/1987 | Bordoloi et al. | 428/345 |
| 4,728,572 | 3/1988 | Davis | 428/355 |
| 4,793,337 | 12/1988 | Freeman et al. | 428/156 |
| 4,814,168 | 3/1989 | Sablotsky et al. | 428/78 |
| 4,831,070 | 5/1989 | McInally et al. | 524/588 |
| 4,865,920 | 9/1989 | Sweet | 428/447 |
| 4,882,377 | 11/1989 | Sweet et al. | 524/267 |
| 4,904,720 | 2/1990 | Kawakatsu et al. | 524/266 |
| 4,988,779 | 1/1991 | Medford et al. | 524/588 |

OTHER PUBLICATIONS

"Customizing Silicone Adhesives for Transdermal Drug Delivery Systems", by William R. Pfister, reprinted from Pharmaceutical Technology, Mar. 1989 (10 pages).

Primary Examiner—Melvyn I. Marquis
Assistant Examiner—Karen A. Hellender
Attorney, Agent, or Firm—Lynn E. Cargill

[57] ABSTRACT

Hot-melt silicone pressure sensitive adhesive compositions, methods of using the compositions, articles made using the compositions, and methods of making articles using the compositions. The hot-melt silicone pressure sensitive adhesive compositions include a mixture of (i) a silicone resin, (ii) a polyolimethylsiloxane fluid, and (iii) from about 0.5 to about 20 weight percent, based on the total weight of the silicone resin and the polydimethylsiloxane fluid, of a polyphenylmethylsiloxane fluid having a viscosity at 25° C. of from about 5 to about 60,000 centistokes so that the adhesive will be in a generally flowing state at temperatures above about 100° C., as well as being capable of transdermal drug delivery.

15 Claims, No Drawings

HOT-MELT SILICON PRESSURE SENSITIVE ADHESIVES WITH PHENYL-CONTAINING SILOXANE FLUID ADDITIVE AND RELATED METHODS AND ARTICLES

This is a continuation of co-pending application Ser. No. 07/508,459 filed on Apr. 13, 1990, now abandoned.

TECHNICAL FIELD

The present invention relates to hot-melt silicone pressure sensitive adhesive compositions, methods of making an article using the compositions, methods of using the composition, and articles made using the composition.

BACKGROUND OF THE INVENTION

A pressure sensitive adhesive, generally, is a material which adheres to a surface with slight pressure and releases from the surface with negligible transfer of the material to the surface. Silicone pressure sensitive adhesives that are known in the art are typically solvent-based adhesives; the solvents are employed primarily to reduce the silicone pressure sensitive adhesive's viscosity to a viscosity which is easily coated onto the substrate of choice, and the solvents are removed after coating. As with any solvent-based pressure sensitive adhesive (PSA), special precautions must be taken to contain and avoid environmental exposure of the solvents and avoid flammable and explosive conditions since many of the solvents used are flammable.

Hot-melt pressure sensitive adhesives are those adhesives, which upon heating, melt to viscosities suitable for coating, but when cooled are generally in a flowless state. The advantages of hot-melt PSA's relative to solvent-based PSA's are known. Namely, the advantages of hot-melt PSA's are that they (1) do not require removal and containment of solvents, (2) do not require special precautions to avoid fires due to the presence flammable solvents, (3) make available coating processes other than those commonly used with solvent-based PSA's and (4) are more easily coated into thick sections with minimal bubbling which often results with solvent-containing PSA's. In addition, hot-melt PSA's have the advantage of not containing solvents which sometimes interfere with the addition of other ingredients to the PSA.

Silicone pressure sensitive adhesives have been found to be preferred over other types of PSA's in many applications, especially in the medical area. For example, silicone pressure sensitive adhesives, due to the fact that they are acceptable for topical use, have found use in transdermal drug delivery applications which involve the adherence of a drug-containing patch to a patient's skin.

U.S. Pat. No. 4,865,920 to Randall P. Sweet, also the inventor of this invention, discloses a method of making hot-melt silicone pressure sensitive adhesives which have the inherent benefits of being composed of silicone and being a hot-melt PSA. In U.S. Pat. No. 4,865,920, the hot-melt silicone pressure adhesive composition consists of (i) a silicone resin, (ii) a silicone fluid, and (iii) 1 to 10 weight percent, based on the total weight of the silicone resin and silicone fluid, of an ester having the formula: R—C(O)OR' wherein R is a monovalent hydrocarbon radical having from 2 to 32 carbon atoms and R' is a monovalent hydrocarbon radical having from 1 to 14 carbon atoms. Although this silicone pressure sensitive adhesive composition has been found to be highly efficacious, it is desirable to have available a hot-melt silicone pressure sensitive adhesive which is more compatible with certain drugs and other organic materials.

It is also desirable that the new hot-melt silicone pressure sensitive adhesive be capable of being substantially transparent and have controllable adhesion, so that the aggressiveness of adhesion can be tailored to the application. For example, in terms of the transdermal drug delivery patch application, it is desired that the PSA exhibit a suitable adherence to the skin so that it remains adhered for the desired amount of time, but is comfortable to the patient upon removal.

SUMMARY OF THE INVENTION

This invention provides a hot-melt pressure sensitive adhesive composition which possesses the benefits of being a hot-melt adhesive and being formed of materials which are highly acceptable in topical applications. The hot-melt silicone pressure sensitive adhesive compositions of this invention are more compatible with certain drugs and other organic materials than are prior art silicone PSA's and the hot-melt PSA of U.S. Pat. No. 4,865,920. The invention also provides a means of controlling the pressure sensitive adhesive properties of tack, adhesion, and release of the composition.

The invention fulfills the foregoing needs by providing a hot-melt silicone pressure sensitive adhesive composition comprising a mixture of (i) a silicone resin and (ii) a silicone fluid, the mixture exhibiting tackiness and adhesiveness, the mixture being blended with (iii) from about 0.5 to about 20 weight percent, based on the total weight of the silicone resin and the silicone fluid, of at least one phenyl-containing polysiloxane fluid having a viscosity at 25° C. of from about 5 to about 60,000 centistokes. The invention also encompasses methods of using the composition, methods of making hot-melt silicone pressure sensitive adhesive-coated substrates, and devices made using the compositions.

DETAILED DESCRIPTION OF THE INVENTION

Generally, the hot-melt compositions of the invention are composed of a silicone pressure sensitive adhesive and at least one phenyl-containing polysiloxane fluid having a viscosity at 25° C. of from about 5 to about 60,000 centistokes. The components of the hot-melt silicone pressure sensitive adhesive other than the phenyl-containing polysiloxane fluid may be selected from various known silicone pressure sensitive adhesives. Typical silicone pressure sensitive adhesives include a volatile organic solvent, such as xylene (which is flammable and requires environmental control), or trichlorotrifluoroethane (which requires environmental control) for reducing the viscosity of the composition to a coatable room-temperature viscosity, and, after coating, the organic solvent is removed by evaporation. The hot-melt silicone pressure sensitive adhesive compositions of this invention do not employ such solvents that are to be removed, but their viscosities are still capable of being reduced to suitable viscosities for coating at elevated temperatures due to the presence of certain phenyl-containing polysiloxane fluids.

Optionally, the hot-melt silicone pressure sensitive adhesive compositions of the invention may include a minor amount of filler, such as an extending or reinforcing filler. It is usually desired that the filler be present in an amount no greater than about 5 weight % based on the total weight of the silicone resin and the silicone fluid.

One suitable class of pressure sensitive adhesives to be employed in the hot-melt compositions of this invention consists of a mixture of (i) a trimethylsilyl-endblocked polysilicate resin such as a silicone resin consisting of a benzene-soluble resinous copolymer containing silicon-bonded hydroxyl radicals and consisting essentially of triorganosiloxy units of the formula $R''''_3SiO_{\frac{1}{2}}$ and tetrafunctionalsiloxy units of the formula $SiO_{4/2}$ in a ratio of about 0.6 to 0.9 triorganosiloxy units for each tetrafunctionalsiloxy unit present in the copolymer, wherein each $R''''$ is a monovalent organic radical independently selected from the group consisting of hydrocarbon radicals of from 1 to 6 inclusive carbon atoms, and (ii) a silanol-endstopped polydiorganosiloxane fluid, e.g. a polydimethylsiloxane fluid. U.S. Pat. No. 2,736,721 to Dexter, et al. and U.S. Pat. No. 2,814,601, to Currie, et al. are hereby incorporated by reference to teach of such or similar pressure sensitive adhesive compositions.

Another class of suitable pressure sensitive adhesives to use according to the invention is that or those similar to that of U.S. Pat. No. 2,857,356, to Goodwin, Jr., which is hereby incorporated by reference. The Goodwin, Jr. patent teaches of silicone pressure sensitive adhesives which consist of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high viscosity organopolysiloxane fluid containing silicon-bonded hydroxy groups.

The silicone resin (i) and the silicone fluid (ii) may optionally be condensed together according to a procedure such as the procedure described in Canadian Patent 711,756 to Pail, which patent is hereby incorporated by reference. In such a condensation reaction, the silicone resin (i) and the silicone fluid (ii) are mixed together in the presence of a catalytic amount of a silanol condensation catalyst, and then the silicone resin (i) and the silicone fluid (ii) are condensed, for example, by heating under reflux conditions for 1 to 20 hours. Examples of silanol condensation catalysts are primary, secondary, and tertiary amines, carboxylic acids of these amines and quaternary ammonium salts.

Another class of suitable pressure sensitive adhesives to use with the phenyl-containing polysiloxane fluid according to the invention are those compositions described in U.S. Pat. Nos. 4,591,622 and 4,584,355 to Blizzard et al., U.S. Pat. No. 4,585,836 to Homan et al., and U.S. Pat. No. 4,655,767 to Woodard et al., which patents are hereby incorporated by reference. Generally, these pressure sensitive adhesives consist of a blend of (i) a silicone resin and (ii) a silicone fluid which are chemically treated to reduce the silicon-bonded hydroxyl content of the blend. These adhesives may optionally be condensed as described immediately above prior to the chemical treatment.

Typically, the most practical pressure sensitive adhesive for use in this invention includes a polydimethylsiloxane as the silicone fluid, since this material is the most economical and the most available of the silicone fluids.

Generally speaking, the silicone resin is employed in amounts from about 40 to about 70 parts by weight in the silicone pressure sensitive adhesive, and the silicone fluid is employed from about 30 to about 60 parts by weight, wherein the total parts of the silicone resin and the silicone fluid is 100 parts. It is usually preferred that the silicone resin be employed from about 50 to about 60 parts by weight, and, correspondingly, the silicone fluid be employed from about 40 to about 50 parts by weight, wherein the total parts by weight equals 100.

The silicone pressure sensitive adhesives used in this invention are not considered to be "silicone rubbers" which generally refer to non-tacky vulcanized rubbers. The most common type of silicone rubber consists of a mixture of a polydimethysiloxane gum, a filler (such as fumed silica or other inorganic, non-resinous material), a crosslinker, and optionally, a catalyst. On the other hand, the silicone pressure sensitive adhesives employed in this invention are tacky (or sticky) to the touch and typically adhere to a substrate after mild pressure is applied. The silicone pressure sensitive adhesives may be cured or "rubberized" after being mixed with the phenyl-containing polysiloxane fluid as discussed below. However, even after the curing, the silicone pressure sensitive adhesive composition is tacky.

Another difference between silicone pressure sensitive adhesives and silicone rubbers lies in the fact that silicone pressure sensitive adhesives are usually fillerless or contain low amounts, e.g., less than about 5 weight %, of fillers, such as fumed silica or other inorganic reinforcing fillers known in the silicone art. On the other hand, silicone rubbers typically contain about 15-35 weight % filler. Fillers are usually not desired in high quantities in silicone pressure sensitive adhesives, because high quantities often cause the silicone pressure sensitive adhesives to lose tack and adhesiveness and to increase in viscosity, making it more difficult to apply a coating of the silicone pressure sensitive adhesive.

The hot-melt silicone pressure sensitive adhesive compositions of the invention are prepared by merely mixing siloxanes (i) and (ii) with the selected phenyl-containing polysiloxane fluid(s). The hot-melt silicone pressure sensitive adhesive compositions are then heated to a coatable viscosity and coated on a substrate. Optionally, the coated compositions may be cured. When the composition is to be cured, the composition may further contain a curing catalyst. It is preferred that such catalysts remain inactive at room temperature and temperatures reached during the hot-melt coating process. Therefore, such catalysts that either become active at temperatures higher than that of the hot-melting temperatures or become active upon exposure to another energy source, e.g., UV light or electron beam radiation, are most suitable.

The process of curing or crosslinking silicone pressure sensitive adhesives is known in the art. For example, see "Silicone Pressure—Sensitive Adhesives" by D.F. Merrill in the *Handbook Of Pressure—Sensitive Adhesive Technology*, edited by D. Satas (Van Nostrand Reinhold, Florence, Ky., 1982), pages 344-352 and "Formulating Silicone Pressure Sensitive Adhesives For Application Performances" by L.A. Sobieski in *Making It Stick in '86*, Advances In Pressure—Sensitive Tape Technology, seminar proceedings (Pressure Sensitive Tape Council, Deerfield, Ill., 1986), pages 1-5, both sources being hereby incorporated by reference.

Appropriate phenyl-containing polysiloxane fluids for this invention include those that are entirely liquid and those that are combinations of liquid and solid phenyl-containing polysiloxane fluids. The phenyl-containing polysiloxane may be straight-chained or branched so long as the viscosity falls in the proper range. These phenyl-containing polysiloxane fluids are suitable for topical (on animal skin) applications, such as in the case of transdermal drug applications.

A suitable range of viscosity at 25° C. of the phenyl-containing polysiloxane fluids used in this invention is from about 5 to about 60,000 centistokes. Although fluids within the full viscosity range, i.e., from about 5 to about 60,000 centistokes, generally provide suitable hot-melt viscosities for handling and coating, it is preferred that the fluid have a viscosity from about 10 to about 200 centistokes at 25° C.

Preferably, the phenyl-containing polysiloxane fluid has from about 1 phenyl group per 100 siloxane units to about 100 phenyl groups per 100 siloxane units, where a siloxane unit includes a silicon atom bonded to two oxygen atoms, each oxygen atom being bonded to another silicon atom. In other words a siloxane unit consists of the unit, $Z_2SiO_{2/2}$, wherein each Z may be the phenyl group, a hydrocarbon group, —OH, or —O—SiR''$_3$ wherein R'' is a monovalent radical independently selected from the group consisting of hydrocarbon radicals having from 1 to 3 carbon atoms inclusive and —OH. When the term "independently selected" is used, it means that each radical (e.g., each R'') may be the same or different. The "$O_{2/2}$" indicates that two oxygens are bonded to the silicon atom and each is shared with another silicon atom.

Suitable phenyl-containing polysiloxanes have the structure:

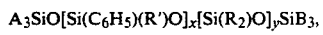

$A_3SiO[Si(C_6H_5)(R')O]_x[Si(R_2)O]_ySiB_3$, wherein each R is a monovalent radical independently selected from the group consisting of —OSiR''$_3$, hydrocarbon radicals having from 1 to 3 carbon atoms inclusive and —OH, each R' is a monovalent radical independently selected from the group consisting of —OSiR''$_3$, —OH, and CH$_3$, each R'' is a monovalent radical independently selected from the group consisting of hydrocarbon radicals having from 1 to 3 carbon atoms inclusive, A and B are independently selected endgroups and x is greater than zero and x and y are average values selected such that the phenyl-containing polysiloxane fluid has a viscosity at 25° C. from about 5 to about 60,000 centistokes and has from about 1 phenyl group per 100 siloxane units to about 100 phenyl groups per 100 siloxane units. A and B may each be one of many suitable endgroups, e.g., —OSiR'''$_3$ where each R''' is a hydrocarbon radical having from 1-8 carbon atoms inclusive, hydrocarbon radicals having from 1-8 carbon atoms inclusive, —OH, halide radicals, or amine radicals. A and B are usually not critical as the relative amount in the overall structure makes their properties of little significance.

A preferred phenyl-containing polysiloxane has the structure:

$(CH_3)_3SiO[Si(C_6H_5)(OSi(CH_3)_3)O]_nSi(CH_3)_3$, wherein n is an average value selected so that the viscosity of the phenyl-containing polysiloxane fluid at 25° C. is from about 5 to about 60,000 centistokes.

Another suitable class of phenyl-containing polysiloxanes has the structure:

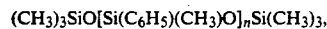

$(CH_3)_3SiO[Si(C_6H_5)(CH_3)O]_nSi(CH_3)_3$, wherein n is an average value such that the viscosity of the fluid at 25° C. is from about 5 to about 60,000 centistokes.

The phenyl-containing polysiloxane fluids for the hot-melt silicone pressure sensitive adhesive compositions of the invention are not flammable which affords a safer procedure during application of the hot-melt silicone pressure sensitive adhesive compositions at elevated temperatures. Flammable materials, as the term is used herein, are those materials which are flammable according to the definition provided in United States Code of Federal Regulations (CFR), Title 49, Part 173, Section 10.5 (49 CFR 173.10.5). Briefly restated, a flammable liquid means any liquid having a flash point below 100° F., where flash point means the minimum temperature at which a liquid gives off vapor within a test vessel in sufficient concentration to form an ignitable mixture with air near the surface of the liquid. The CFR provides proper testing conditions for measuring flash point. If flammable materials are included in the composition, the coating operation could be done in an inert atmosphere (e.g. nitrogen gas), devoid of combustible gas to avoid fire hazards.

The phenyl-containing polysiloxane fluid employed must not vaporize significantly at the processing temperatures. Typically, temperatures above about 100° C. produce suitable working viscosities with the compositions of this invention, therefore, phenyl-containing polysiloxane fluids having boiling points above 100° C. are preferred.

The phenyl-containing polysiloxane fluids may be employed in amounts of about 0.5 to 20 weight percent based on the total weight of the silicone resin and the silicone fluid. Preferably, the phenyl-containing polysiloxane fluid is employed from about 10 to about 15 weight percent. At the higher amounts, especially with low molecular weight phenyl-containing polysiloxane fluids, the hot-melt silicone pressure sensitive adhesive composition may be quite flowable at room temperature which is undesirable for many PSA applications. This problem may be overcome, however, by curing the PSA after coating as discussed earlier.

The hot-melt silicone pressure sensitive adhesive compositions of this invention may be made by mixing the ingredients in any order. Reaction or treatment of the ingredients, e.g., condensing according to the procedure of the previously-mentioned Pail patent or chemically treating according to the previously-mentioned Blizzard et al., etc. patents may require completion prior to the addition of the phenyl-containing polysiloxane fluid.

The inclusion of the phenyl-containing polysiloxane fluid allows the hot-melt silicone pressure sensitive adhesive composition to decrease in viscosity at elevated temperatures to a suitable viscosity for coating a substrate without the use of solvents that must be removed. Suitable viscosities for hot-melt processing vary depending on the equipment used, the thickness of the coating desired, and the desired speed of coating, etc.

When using the hot-melt silicone pressure sensitive adhesive compositions of this invention to coat a substrate, the method comprises the steps of (a) heating the hot-melt silicone pressure sensitive adhesive composition to a coatable temperature above 25° C., (b) coating the heated hot-melt silicone pressure sensitive adhesive composition onto the substrate, and (c) cooling the coated hot-melt silicone pressure sensitive adhesive composition until it is in a generally non-flowing state.

Typically, heating the hot-melt silicone pressure sensitive adhesive compositions of this invention to temperatures of about 100° C. or more (more typically about 150° C.) results in suitable viscosities. These coatable temperatures are low enough so that decomposition of the composition does not occur. Lower temperatures may result in coatable viscosities depending on the coating equipment used, the desired end product, and the composition of the hot-melt silicone pressure sensitive adhesive composition. For example, the thicker the layer of pressure sensitive adhesive desired, the higher the coating viscosity can be.

When the hot-melt silicone pressure sensitive adhesive compositions are applied to a backing or substrate, this procedure may be accomplished by using any conventional means, such as, roller coating, dip coating, extrusion, knife coating, or spray coating.

The hot-melt silicone pressure sensitive adhesive compositions of the invention will adhere to many substrates, such as paper, cloth, glass cloth, silicone rubber, polyethylene, polyethylene terephthalate, polytetrafluoroethylene, glass, wood, metals, and skin. Therefore, there are many uses for the hot-melt silicone pressure sensitive adhesive compositions of this invention. Depending on the desired use, it may be desirable to apply adhesion promoters on the substrate surface upon which the hot-melt silicone pressure sensitive adhesive composition will be placed.

The hot-melt silicone pressure sensitive adhesive compositions of this invention are especially suitable for assisting in delivering a bioactive agent, such as a drug, to a bioactive agent-accepting substrate, such as a patient's skin. The hot-melt silicone pressure sensitive adhesive compositions of this invention may be employed in two types of bioactive agent delivery modes. One mode is by incorporating the bioactive agent in the hot-melt silicone pressure sensitive adhesive composition which is thereafter attached to the substrate to commence delivery. The second mode of delivery is by attaching a membrane of a material, optionally, of the hot-melt silicone pressure sensitive adhesive composition of this invention, to the substrate using the hot-melt silicone pressure sensitive adhesive composition of this invention, and, then, contacting a reservoir of a bioactive agent to the attached membrane. The bioactive agent may then pass from the reservoir through the attached membrane and to the substrate for absorption. For this mode, a bioactive agent delivery device may be made which includes (a) a container, (b) a bioactive agent contained in the container, and (c) a hot-melt silicone pressure sensitive adhesive composition of this invention on the container for providing a means for adhering the container to the bioactive agent-accepting substrate.

Due to the presence of the phenyl-containing polysiloxane fluid in the hot-melt silicone pressure sensitive adhesive compositions of this invention, certain drugs and other organic materials are more compatible in the compositions than in prior art compositions. One way to determine if a material is more compatible in the compositions of this invention as compared to PSA's containing only dimethylsiloxane fluids is to refer to Hildebrand solubility parameters which are well known in the art. The Hildebrand solubility parameter for $(CH_3)_2SiO$-based fluids is 7.38 whereas the Hildebrand solubility parameter for $(C_6H_5)(CH_3)SiO$-based fluids is 9.76. Therefore, drug compounds or excipients that have solubility parameters above 9.76 (i.e., are more hydrophilic) will have greater compatibility and will provide higher drug release rates with the compositions of this invention as compared to the typical fully dimethylsiloxanebased PSA's. Drugs such as estradiol, norethindrone, cortisol, prednisolone, and estriol are more soluble in the PSA's of the invention than in typical silicone PSA's. Organic materials such as stearyl alcohol, beeswax, lanolin, mineral oil, paraffin, petrolatum, and isopropyl myristate are more compatible in the compositions of this invention than they would be in compositions without the phenyl-containing polysiloxane.

Improved compatibility may mean that a higher amount of a substance may be added to a composition without separation of the substance from the composition. Additionally or alternatively, improved compatibility may mean that an added substance does less to disrupt the physical properties of a composition.

In addition, the hot-melt silicone pressure sensitive adhesive compositions of this invention have the potential advantage, when used in transdermal drug delivery applications, to provide additional benefits in terms of providing an improved control of permeation rates of the drug through the skin.

The following examples of the invention are meant to be illustrative only and should not be construed as limiting the invention which is properly delineated in the appended claims. In the following examples, all parts and percentages are by weight unless otherwise specified.

"N.V.C." (Nonvolatile Content) of a resin, as given below, was determined by mixing 1.5 g of the resin with 0.75 g. of a 100 cSt. viscosity trimethylsiloxy-endblocked polydimethylsiloxane (PDMS) fluid in an aluminum foil dish, 60 mm in diameter and 15 mm deep, and heating the sample for 2 hours at 150° C. in an air-circulating oven. The heated sample was then cooled to room temperature and reweighed to determine the weight of the nonvolatile material (w). The N.V.C., in percent, is equal to $100 \times w/1.5$.

For the following examples, Resin A-1 is a xylene solution of a resinous copolymeric siloxane prepared from 45 parts of sodium silicate (41.6° Be) and 20 parts of $Me_3SiCl$ ($Me=CH_3$) according to the method of U.S. Pat. No. 2,676,182 to Daudt, et al., which is hereby incorporated by reference, and contains $Me_3SiO_{\frac{1}{2}}$ units and $SiO_{4/2}$ units in a ratio of approximately 0.75:1.0, and has a N.V.C. typically about 69–71%, an acid number in the range of 0.3 to 1.4, a viscosity in the range of 10–14 centipoise at 25° C. at 60% N.V.C. in xylene solution, and a silicon-bonded hydroxyl content of about 2.5 weight percent based on a 100% N.V.C.

Resin A-2 is devolatilized Resin A-1 (100% nonvolatile content).

PDMS Fluid A is a homogeneous mixture of a hydroxyl-endblocked polydimethylsiloxane having a number-average molecular weight of approximately 40,000 and minor amounts of cyclic polydimethylsiloxane having degrees of polymerization between 4 and 30, the mixture having a viscosity between 12,000 and 15,000 centipoise as measured using a Brookfield Viscometer Model HAF with spindle #3 at 10 RPM's.

PSA A was prepared by homogeneously mixing 24.1 parts by weight of Resin A-2, 39.8 parts by weight xylene, and 36.1 parts by weight PDMS Fluid A. The mixture was then heated to 100° C. and anhydrous ammonia was passed through the mixture at a rate of 11 ml/min/lb of non-volatile component of the mixture for 2 hours. To endcap the mixture, hexamethyldisilazane was then admixed at a 3:1 mole ratio of endblocking triorganosilyl to total silicon-bonded hydroxyl radicals present in the resin copolymer and polydiorganosiloxane, and the mixture was allowed to react for 3 hours at 95°-100° C. The mixture was then heated to 140° C and maintained at 140° C. under reflux conditions for 3 hours to remove condensation water. The mixture was then stripped to greater than 90% non-volatile content.

PSA B is a pressure sensitive adhesive composition prepared by homogeneously mixing 60 parts of Resin A-1, 40 parts of PDMS Fluid A, and a portion of 2.4 parts of ammonium carbonate, heating the mixture to 100° C. and maintaining the temperature at 100° C. for 1 hour. Then the remaining portion of the 2.4 parts ammonium carbonate were added to the mixture, and mixing continued for another hour at 100° C. The mixture was then stripped for 16 hours at 100° C. to remove the volatile components. PSA B cooled to room temperature had (1) a specific gravity of 1.085-1.115, (2) a N.V.C. of at least 98.8% where N.V.C. is defined as above except that a 1 g. sample was used and the temperature of the oven was 177° C., (3) a plasticity of $150-200 \times 10^{-3}$ inches as measured after a 24 hour rest and after force was applied on a 2 gram specimen 20 for 3 minutes $+/-5$ seconds using ASTM D926, and, (4) when dispersed in trichlorotrifluoroethane to an N.V.C. of 18.5%, the adhesive peel measured at least 1600 g.

PSA C was prepared by the method described for preparing PSA B except that 55 parts by weight of Resin A-1 and 45 parts by weight of PDMS Fluid A were used instead of the amounts given for PSA B.

Phenyl Fluid A is a polyphenylmethylsiloxane copolymer fluid having the following structure:

wherein n is an average value such that the viscosity of the fluid is about 22.5 centistokes at 25° C. as measured with a Brookfield Viscometer. The flash point (closed cup test) of Phenyl Fluid A is about 250° F.

Phenyl Fluid B is a phenyl-methyl-silicone oil having the structure:

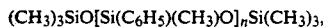

wherein n is an average value such that the viscosity of the fluid at 25° C. is about 125 centistokes as measured with a Brookfield Viscometer Model RVT, using a No. 3 spindle at 100 rpm's.

EXAMPLES 1-12

In Examples 2-4, 6-8, and 10-12, hot-melt silicone pressure sensitive adhesive compositions were prepared by mixing the compositions indicated in Table 1 at about 100° C.-150° C. until homogeneously mixed and then allowing the mixture to cool to room temperature. Compositions of Examples 6-8 and 10-12 were transparent, thus, indicating that Phenyl Fluid A is quite compatible with PSA's B and C. Compositions of Examples 2-4 were milky in appearance, thus, indicating that Phenyl Fluid B is not fully compatible with PSA A. Examples 1, 5, and 9 are provided to show the properties of the various silicone pressure sensitive adhesives without the added phenyl-containing polysiloxane fluid when the data was available.

TABLE 1

| Example # | PSA Type Employed | Phenyl Fluid Employed | Weight % Phenyl Fluid Employed* |
|---|---|---|---|
| 1 | PSA A | none | 0 |
| 2 | PSA A | B | 5 |
| 3 | PSA A | B | 10 |
| 4 | PSA A | B | 15 |
| 5 | PSA B | none | 0 |
| 6 | PSA B | A | 5 |
| 7 | PSA B | A | 10 |
| 8 | PSA B | A | 15 |
| 9 | PSA C | none | 0 |
| 10 | PSA C | A | 1 |
| 11 | PSA C | A | 5 |
| 12 | PSA C | A | 10 |

*Based on the total weight of the silicone fluid and silicone resin in the PSA composition.

Dynamic viscosities (n*) and elastic storage moduli (G') were measured on some of the compositions using a Visco-Elastic Tester available from Rheometrics, Piscataway, N.J., and running a temperature sweep on 10 gram samples and operating the tester at a frequency of 10 rad/sec and a 1% strain using a 50 mm cup and plate.

Elastic storage modulus is directly related to die swell and elastic memory. The higher the die swell, the smaller the size of an orifice required for a given coating thickness. Therefore, the lower the elastic storage modulus, the better, as it is then easier to coat onto a substrate. Tests similar to those run in these examples are described in ASTM 4065-82. The viscosities and elastic storage moduli of the compositions measured are given in Tables 2 and 3, respectively. In the tables, "ND" refers to "Not Determined". All of the examples of this invention had suitable viscosities for hot-melt coating at least at 200° C.

TABLE 2

| | Dynamic Viscosity (poise) | | |
|---|---|---|---|
| Example # | 30° C.* | 100° C.* | 200° C.* |
| 1 | 563,700 | 45,420 | 1,050 |
| 2 | 506,600 | 25,160 | ND |
| 3 | 382,000 | 11,660 | ND |
| 4 | 284,200 | 8,147 | ND |
| 5 | ND | ND | ND |
| 6 | 3,262,000 | 96,000 | 1,315 |
| 7 | 903,400 | 40,000 | 1,186 |
| 8 | 266,800 | 15,000 | 722 |

*Temperatures are approximate. Actual temperatures ranged from 27 to 30 for the 30° C. column, from 95 to 104 for the 100° C. column, and from 195 to 200 for the 200° C. column.

TABLE 3

| | Elastic Storage Modulus dynes/cm² | | |
|---|---|---|---|
| Example # | 30° C.* | 100° C.* | 200° C.* |
| 1 | 5,570,000 | 180,000 | 2,700 |
| 2 | 4,805,000 | 123,500 | ND |
| 3 | 3,274,000 | 52,990 | ND |
| 4 | 2,186,000 | 35,050 | ND |
| 5 | ND | ND | ND |
| 6 | 2,744,000 | 40,000 | 1,200 |
| 7 | 560,400 | 18,000 | 181 |
| 8 | 153,900 | 5,600 | 22 |

*Temperatures are approximate. Actual temperatures ranged from 27 to 30 for the 30° C. column, from 95 to 104 for the 100° C. column, and from 195 to 200 for the 200° C. column.

Tapes were prepared from some of the hot-melt silicone pressure sensitive adhesive compositions of these examples to measure tack, adhesion and release values. The selected compositions were casted to a 2 mil thickness onto one-inch wide strips of SCOTCH-PAK 1022 Release Liner, a polyester film coated with a release coating available from the 3M Company, St. Paul, Minn., using a hot melt coater manufactured by Bushman Corporation, Kirtland, Ohio, operated at a temperature of about 150° C. After coating, a one-inch wide strip of MYLAR polyester film was adhered to each casted sample with a 4 lb. roller.

The release values were obtained by stripping the tape from the SCOTCH-PAK 1022 Release Liner at a rate of 40 inches/minutes at an angle of 180° while attached to a tensile testing machine, with the results being expressed in grams per centimeter. An average value over the entire length of the liner was recorded.

The tapes (2 mil thick hot-melt pressure sensitive adhesive composition on MYLAR) were then each adhered to a stainless steel panel with a 4 lb. roller and allowed to rest for 15 minutes. The adhesion measurements were obtained by stripping each tape from the panel at a rate of 12 inches/minute at an angle of 180° while attached to a tensile testing machine, with the results expressed in grams per centimeter.

Tack was measured in grams using a POLYKEN Probe Tack Tester, Series 400, made by Testing Machines, Inc., Amityville, N.Y. The speed of the probe was 0.5 cm/second and the dwell time of the probe was 0.5 seconds. The tack, adhesion and release values of the selected compositions are given in Table 4.

TABLE 4

| Example # | Tack grams | Adhesion To | |
|---|---|---|---|
| | | Release g/cm | Stainless Steel g/cm |
| 9 | 524 | 10 | 555 |
| 10 | 615 | 11 | 474 |
| 11 | 784 | 14 | 492 |
| 12 | 903 | 14 | 482 |

These and other variations of the present invention may be made which fall within the scope of the appended claims even though such variations were not specifically discussed above.

That which is claimed is:

1. A hot-melt silicone pressure sensitive adhesive composition, comprising a mixture of
   (i) a silicone resin and
   (ii) a polydimethylsiloxane fluid, said mixture exhibiting tackiness and adhesiveness, said mixture being blended homogeneously with
   (iii) from about 0.5 to about 20 weight percent, based on the total weight of said silicone resin and said polydimethylsiloxane fluid, of polyphenylmethylsiloxane copolymer fluid, $(CH_3)_3SiO[Si(C_6H_5)(OSi(CH_3)_3)O]_nSi(CH_3)_3$, where n is selected so that the viscosity of the homogeneously blended mixture is from about 5 to about 60,000 centistokes so that the adhesive will be in a generally flowing state at temperatures above about 100° C., as well as being capable of transdermal drug delivery.

2. The hot-melt silicone pressure sensitive adhesive composition as claimed in claim 1, wherein said silicone resin is employed in an amount from about 40 to about 70 parts by weight, and said polydimethylsiloxane fluid is employed in an amount from about 30 to about 60 parts by weight, wherein the total parts of the silicone resin and the polydimethylsiloxane fluid equal 100.

3. The hot-melt silicone pressure sensitive adhesive composition as claimed in claim 1, wherein said silicone resin is employed in an amount from about 50 to about 60 parts by weight, and said polydimethylsiloxane fluid is employed in an amount from about 40 to about 50 parts by weight, wherein the total parts of the silicone resin and the polydimethylsiloxane fluid equal 100.

4. The hot-melt silicone pressure sensitive adhesive composition as claimed in claim 1, wherein the hot-melt silicone pressure sensitive adhesive is fillerless.

5. The hot-melt silicone pressure sensitive adhesive composition as claimed in claim 1, wherein the hot-melt silicone pressure sensitive adhesive composition contains less than about 5 weight % of an inorganic filler.

6. The hot-melt silicone pressure sensitive adhesive composition as claimed in claim 1, wherein said hot-melt silicone pressure sensitive adhesive composition is nonflammable.

7. A method of making a hot-melt silicone pressure sensitive adhesive-coated substrate, comprising:
   (a) heating, to a coatable temperature above 100° C., a hot-melt silicone pressure sensitive adhesive composition which includes a mixture of
       (i) a silicone resin and
       (ii) a polydimethylsiloxane fluid, said mixture exhibiting tackiness and adhesiveness, said mixture being blended with
       (iii) from about 0.5 to about 20 weight percent, based on the total weight of said silicone resin and said polydimethylsiloxane fluid, of a phenyl-containing polysiloxane fluid having a viscosity at 24° C. of from about 5 to about 60,000 centistokes,
   (b) coating said heated hot-melt polydimethylsiloxane pressure sensitive adhesive composition onto a substrate, and
   (c) cooling the coated hot-melt silicone pressure sensitive adhesive composition until it is in a generally non-flowing state.

8. The method as claimed in claim 7, wherein said silicone resin is employed in an amount from about 40 to about 70 parts by weight, and said polydimethylsiloxane fluid is employed in an amount from about 30 to about 60 parts by weight, wherein the total parts of the silicone resin and the polydimethylsiloxane fluid equal 100.

9. The method as claimed in claim 7, wherein said silicone resin is employed in an amount from about 50 to about 60 parts by weight, and said polydimethylsiloxane fluid is employed in an amount from about 40 to about 50 parts by weight, wherein the total parts of the silicone resin and the polydimethylsiloxane fluid equal 100.

10. The method as claimed in claim 7, wherein the hot-melt silicone pressure sensitive adhesive composition is fillerless.

11. The method as claimed in claim 7, wherein the hot-melt silicone pressure sensitive adhesive composition contains less than about 5 weight % of an inorganic filler.

12. The method as claimed in claim 7, wherein said hot-melt silicone pressure sensitive adhesive composition is nonflammable.

13. The method as claimed in claim 7, wherein said coatable temperature is above 100° C.

14. The method as claimed in claim 7, wherein said coatable temperature is above 150° C.

15. The hot-melt silicone pressure sensitive adhesive of claim 1, further comprising a bioactive agent having a Hildebrand solubility parameter above 9.76.

* * * * *